United States Patent
Snay et al.

(10) Patent No.: US 7,118,569 B2
(45) Date of Patent: Oct. 10, 2006

(54) BIPOLAR RESECTOSCOPE ELECTRODE

(75) Inventors: James P. Snay, Republic, OH (US); Michael D. Blaisdell, Willard, OH (US)

(73) Assignee: ACMI Corporation, Southborough, MA (US)

( * ) Notice: Subject to any disclaimer, the term of this patent is extended or adjusted under 35 U.S.C. 154(b) by 84 days.

(21) Appl. No.: 10/838,507

(22) Filed: May 3, 2004

(65) Prior Publication Data

US 2005/0245927 A1 Nov. 3, 2005

(51) Int. Cl.
*A61B 18/18* (2006.01)

(52) U.S. Cl. .............................. 606/46; 606/48; 606/50

(58) Field of Classification Search .................. 606/46, 606/48, 50
See application file for complete search history.

(56) References Cited

U.S. PATENT DOCUMENTS

| | | | | |
|---|---|---|---|---|
| 3,149,633 A | * | 9/1964 | Zingale | 606/46 |
| 4,060,087 A | * | 11/1977 | Hiltebrandt et al. | 606/46 |
| 5,047,027 A | * | 9/1991 | Rydell | 606/48 |
| 5,192,280 A | | 3/1993 | Parins | |
| 5,197,964 A | * | 3/1993 | Parins | 606/48 |
| 5,201,732 A | | 4/1993 | Parins et al. | |
| 5,683,387 A | * | 11/1997 | Garito et al. | 606/45 |
| 5,810,764 A | * | 9/1998 | Eggers et al. | 604/23 |
| 5,919,191 A | * | 7/1999 | Lennox et al. | 606/48 |
| 5,976,129 A | * | 11/1999 | Desai | 606/40 |
| 5,993,445 A | * | 11/1999 | Issa | 606/46 |
| 6,322,494 B1 | * | 11/2001 | Bullivant et al. | 600/104 |
| 6,352,533 B1 | * | 3/2002 | Ellman et al. | 606/41 |
| 6,395,001 B1 | * | 5/2002 | Ellman et al. | 606/41 |
| 6,471,701 B1 | | 10/2002 | Brommersma et al. | |
| 6,562,036 B1 | * | 5/2003 | Ellman et al. | 606/45 |
| 6,620,156 B1 | * | 9/2003 | Garito et al. | 606/32 |
| 2004/0199159 A1 | * | 10/2004 | Lee et al. | 606/47 |

* cited by examiner

*Primary Examiner*—Michael Peffley
*Assistant Examiner*—Alex Toy
(74) *Attorney, Agent, or Firm*—Ganz Law, P.C.

(57) ABSTRACT

An electrode assembly is provided having an active power element and a current return element extending through a flexible multilumen tube to be electrically insulated from each other. The active power element extends through the multilumen tube and terminates in a "J-hook" and is connected to a conductive power contact through a constructed form fit. The return element extends through the multilumen tube and directly connects to a power return contact, thus eliminating any joints in the electrical path.

18 Claims, 1 Drawing Sheet

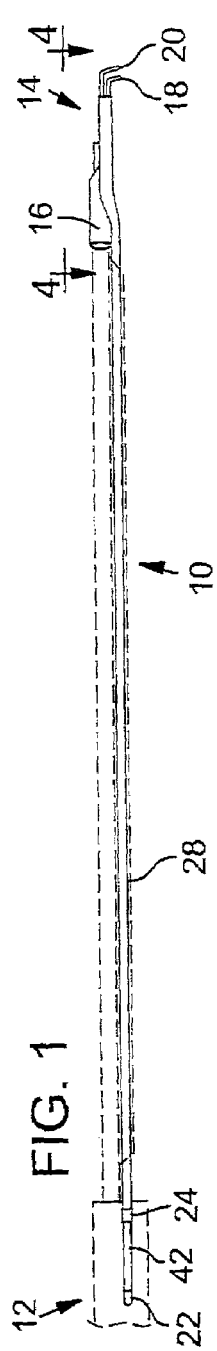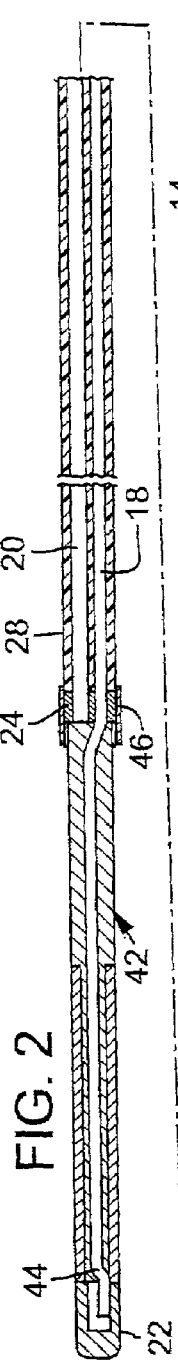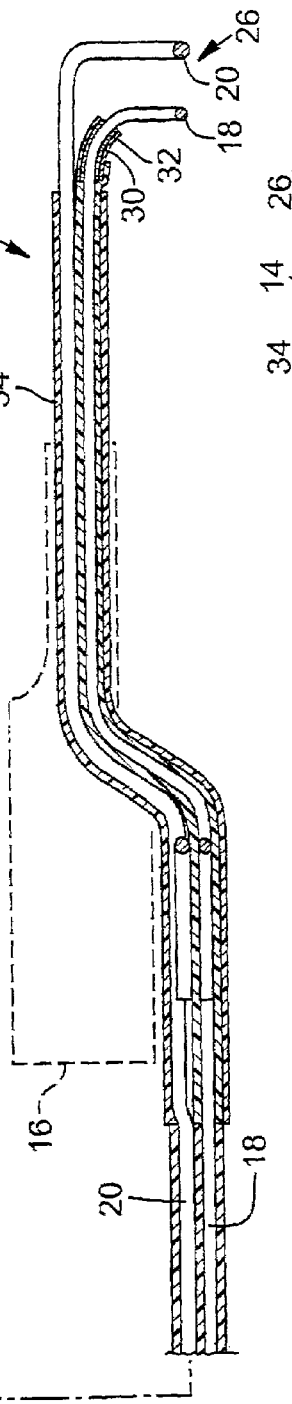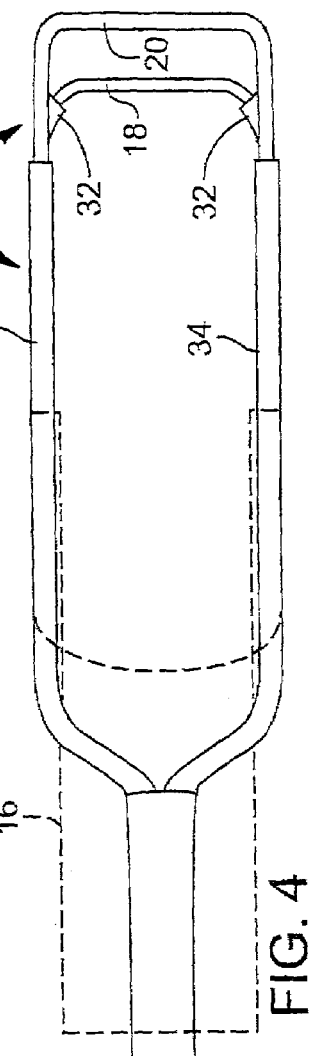

BIPOLAR RESECTOSCOPE ELECTRODE

BACKGROUND OF THE INVENTION

This invention is directed to resectoscopes and, more particularly, to an improved electrode assembly for use with resectoscopes. Such electrodes may be monopolar or bipolar. Monopolar probes include a single active electrode introduced into a body cavity to be engageable with and insertable into a tissue portion of the body cavity. A passive electrode is attached to the outer body surface of the patient and a conducting plate is typically adhesively attached to the patient's leg. The patient's body serves to complete the electrical circuit. Tissue ablation and coagulation is achieved by introducing sufficient power into the active electrode. Bipolar electrode probes include both active and passive electrodes that are similarly introduced together into the body cavity and are spaced apart from each other by a predetermined distance. Each electrode is engageable with and insertable into the tissue portion. The electrical circuit is completed by the body tissue disposed between the active and the passive electrodes. However, the construction of such prior art devices do not provide reliability and safety. Many devices include plural joints in the electrical path. Each joint adds resistance to the electrical path. Therefore, the power source is then required to have an initial output voltage to overcome the resistance. This may lead to misfiring or delayed firing.

For example, one known prior art device includes an electrode having a power element and a return element that form a cutting loop. The return element extends from the cutting loop and is spot-welded to a stainless steel sleeve forming an intermediate joint. Proximally to that joint the sleeve is slip fitted to a stainless steel return contact. Both the active and return elements reside in the single lumen formed by the stainless steel sleeve. Because of the sleeve's stainless steel construction the sleeve does not afford flexibility. This device also terminates proximally in a contact in communication with a power source. The contact comprises a straight section of tungsten wire epoxied into a brass fitting. The construction of this device does not provide optimal operation. More specifically, the intermediate joint in the current path formed by the stainless steel sleeve connection with the return element, the lack of separate lumens, and the epoxied wire in proximal contact for the power element cause this device to be more prone to shorting and failure.

Another device is shown and described in U.S. Pat. No. 5,810,764, in which a bipolar loop electrode device for use with a resectoscope is disclosed. In one embodiment, a return electrode is incorporated in the loop electrode assembly as an electrically conducting shaft covered with an insulating layer. The distal end of the shaft is exposed for completing the return path with active electrode assembly. The proximal end is also exposed to connect the electrode to a power supply. The loop portion of the assembly has a proximally extending electrical connection. The connection may be wires, metal tubes, or the like. The electrical connection extends through the shaft to a connector leg at the proximal end of the assembly. The electrical connections are connected to the electrode using crimping, soldering, or welding. This device uses tubing to conduct power making the device stiff causing higher actuation forces in the working element. Additionally, using the tubing to conduct power makes electrical conduction more difficult increasing the chances for misfire or delayed firing.

Another prior art device is shown and described in U.S. Pat. No. 5,976,129, in which a bipolar electrode assembly includes an active electrode loop and a return electrode loop. Each electrode is contained in a separate guide sheath to extend from the distal end of the device to the proximal end to connect to a power supply. The connections for the return and active electrodes are located in a common, two-prong plug. This device uses a roller to coagulate blood after cutting. The device must be energized through an external source. Additionally, this device includes complicated electrical connections that may lead to misfiring and delayed firing.

Another prior art device is shown and described in U.S. Pat. No. 5,201,732, in which a bipolar sphincterotomy device includes a pair of conductive wires. The wires extend from the distal end of the device to provide bipolar electrode surfaces. To prevent shorting, each wire may be disposed in a separate lumen of a flexible elongate tubular member and run as uninterrupted wires from the distal to proximal end of the device. However, this device does not disclose a wire loop and is not suitable for use with a resectoscope. Additionally, the number of electrical connections may increase the risk of misfiring.

Another prior art device is shown and described in U.S. Pat. No. 5,047,027, in which a bipolar electrosurgical device for tumor resection is disclosed. The device has wires that may be disposed in separate lumens of a flexible elongate tubular member and run as uninterrupted wires from the distal to proximal end of the device. The device has an active electrode in the form of a circular loop at the distal end of the device. The return electrode has a spiral wound configuration proximal to the distal electrode. This device poses a shock hazard to the patient because there is nothing to complete the electrical circuit. Furthermore, the device includes electrical connections that increase the risk for misfiring.

Another prior art device is disclosed in U.S. Pat. No. 5,192,280, which shows and describes parallel loop-like bipolar electrodes at the distal end of an electrosurgical device. The device is intended for use in transuretheral resectioning of the prostate. Wires for each electrode pass through a ceramic head member at the distal end of the device and are joined to the electrodes at two points. Proximal to the connection points the wires are disposed in a common lumen. This device is not constructed to perform electrosurgical cutting without secondary movement and is not user friendly.

Another prior art device is disclosed in U.S. Pat. No. 6,471,701, which shows and describes a bipolar electrode assembly for use with a resectoscope. The electrode assembly includes a cutting loop. A convex insulator is mounted between the arms of the loop. The assembly includes a neutral (return) electrode that has an exposed conductive surface. Conductors connect the active and return electrodes to the terminals of the power source. The conductors are contained in the tube forming a single lumen. This device includes multiple contacts increasing the number of joints in the electrical path.

None of the prior art devices disclose a bipolar electrode for use with a resectoscope that provides flexibility yet is constructed to prevent shorting and failure.

SUMMARY OF THE INVENTION

The present invention overcomes the deficiencies of prior art devices by providing an electrode assembly that provides flexibility during operation yet is safe and reliable.

The present invention provides an electrode assembly having a distal working loop or having an active power element and a current return element. In the preferred embodiment, both the power and return elements are configured as loops, with the return element being distally spaced from the power element. The power element and the return element each extend proximally from the loops and through a flexible multilumen tube so that the power element and return element are electrically insulated from each other. The multilumen tube is made from a flexible material, which allows greater freedom for the electrode to conform to the surgical environment.

The return element extends proximally through the flexible tube and terminates at a return contact for return of current located distally of the proximal end of the device. The power element also extends proximally through the flexible tube and terminates at the proximal end of the electrode. The proximal end of the power element is connected to a power contact with a constructed form joint. Preferably, the power element is made of tungsten, which provides desirable electrosurgical cutting properties. The power contact is preferably made of brass because brass is highly conductive. The power contact and is deformed or crimped to the power element. Tungsten is difficult to mate with brass or other contact metals because tungsten is much harder than brass or other suitable contact metals. The invention's arrangement of constructing the tungsten power element and the brass power contact into a form joint provides an improved contact that is less vulnerable to delayed firing, shorting, and failing.

This invention overcomes the problems of the prior art by eliminating joints in the current path resulting in a system having less than 1 Ohm of resistance. This invention further provides reliability and safety by electrically separating the power element and return element, providing flexibility via the multilumen tube, and providing direct mating of the power element to the power contact to form the proximal contact.

This invention provides an electrode assembly for use with an electrosurgical instrument having an elongate flexible shaft having a proximal end and a distal end with a first electrode located within the shaft. The first electrode has a distal end and a proximal end with the distal end being formed in a loop to apply electrical energy to a body of a patient. A second electrode is located within the shaft having a distal end and a proximal end with its distal end being formed in a loop spaced from the first electrode. The first and second electrodes are electrically insulated from each other. A power contact is located at the proximal end of the shaft connected to the proximal end of the first electrode and a current return contact is directly connected to the proximal end of the second electrode. The proximal end of the first electrode is connected to the power contact with a constructed form joint.

The present invention further provides an electrode assembly for use with an electrosurgical instrument having an elongate flexible shaft with separate first and second lumens with a proximal end and a distal end. The shaft includes a first contact and a second contact for connection with a power source. A first electrode is located within the first lumen. The first electrode has a distal end formed in a loop to apply electrical energy to a body of a patient and a proximal end connected to the first contact for connection with the power source. A second electrode is located within the second lumen. The second lumen has a distal end formed in a loop distally spaced from the first electrode and a proximal end directly connected to the second contact and the second contact is distally located from the first contact.

A method of making an electrode assembly for use with an electrosurgical instrument is provided comprising the steps of providing an elongate flexible shaft having a proximal end and a distal end, providing a first electrode located within the shaft having a distal end and a proximal end, the distal end of the first electrode being formed in a loop to apply electrical energy to a body of a patient, providing a second electrode located within the shaft having a distal end and a proximal end; the distal end of the second electrode being formed in a loop distally spaced from the first electrode, the second electrode being electrically insulated from the first electrode, providing a current return contact connected to the proximal end of the second electrode, and providing a fitting located at the proximal end of the shaft connected to the proximal end of the first electrode, wherein the proximal end of the first electrode is connected to the fitting with a constructed form joint.

A method of making an electrode assembly for use with an electrosurgical instrument is provided comprising the steps of providing an elongate flexible shaft having separate first and second lumens with a proximal end and a distal end; the shaft including a first contact and a second contact for connection with a power source, providing a first electrode located within the first lumen having a distal end formed in a loop to apply electrical energy to a body of a patient and a proximal end connected to the first contact for connection with the power source, and providing a second electrode located within the second lumen having a distal end formed in a loop distally spaced from the first electrode and a proximal end directly connected to the second contact; wherein the second contact is distally located from the first contact.

These and other embodiments are described in more detail in the following detailed descriptions and the figures.

The foregoing is not intended to be an exhaustive list of embodiments and features of the present invention. Persons skilled in the art are capable of appreciating other embodiments and features from the following detailed description in conjunction with the drawings.

BRIEF DESCRIPTION OF THE DRAWINGS

FIG. 1 is a side view of a preferred embodiment of an electrode assembly according to this invention.

FIG. 2, is a broken cross-sectional view of the electrode assembly of FIG. 1.

FIG. 3 is a cross-section view of the tube member without the power element and return element.

FIG. 4 is a partial top view of the distal end of the electrode assembly.

DETAILED DESCRIPTION OF THE INVENTION

Representative embodiments of the present invention are shown in FIGS. 1–4, wherein similar features share common reference numerals.

FIG. 1 shows a preferred embodiment of an electrode assembly 10 for an electrosurgical resectoscope. Electrode assembly 10 includes a proximal portion 12 and a distal portion 14. Proximal portion 12 is adapted to be received in a jack on a conventional electrosurgical resectoscope (shown in phantom) to apply electrical energy to the body of a patient for tissue ablation and coagulation, for example. Electrode 10 includes a connector element 16 for connection with the resectoscope in a known manner. A power element 18 and a return element 20 are introduced together into the body. Power element 18 and return element 20 are engageable with and insertable into the body tissue. Electrical energy is applied to the body through power element 18 that receives power through a conductive power contact 22 from a power source (not shown). Electrical energy returns through return element 20 to a conductive power return contact 24 in a known manner. The electrical circuit is completed by the body tissue disposed between power element 18 and return element 20.

As seen most clearly in FIGS. 2–4, power element 18 and return element 20 are spaced apart from each other by a predetermined distance. At distal portion 14 power element 18 and return element 20 are exposed to form a working end that may be in the form of a conductive dual loop 26 to apply electrical energy to the target site. A loop may have a continuous or an irregular configuration. Power element 18 and return element 20 extend proximally through a flexible multilumen tube 28 to proximal portion 12. Power element 18 and return element 20 are electrically insulated from each other. At distal portion 14 power element 18 extends through an insulating tube 30. Preferably, insulating tube 30 is made of silicon but may be made of other materials having insulating properties. Insulating tube 30 is surrounded by another insulating material 32 such as polyolefin. Power element 18 and return element 20 are further insulated with a common layer of insulation 34, which may also be a polyolefin material.

Power element 18 and return element 20 are separately sheathed in separate lumens in multilumen tube 28 so that they are electrically isolated from each other. As best seen in FIG. 3, multilumen tube 28 includes a first lumen 36 in which power element 18 is received and a second lumen 38 that receives return element 20. Preferably, multilumen tube 20 is made of a flexible material such as nylon 12, for example, to provide flexibility to allow electrode assembly 10 to conform to the surgical environment. Although nylon 12 is given as one example of material it is understood that other suitable materials may be used. In order to provide further electrical insulation each lumen 36, 38 is coated with a layer 40 of a polyimide or other suitable insulating material.

As best seen in FIG. 2, power element 18 extends out through multilumen tube 28 and through an insulated portion 42 that may include one or more insulating materials. Power element 18 terminates at a proximal end 44 that is deformed preferably into a "J-hook" for connection with power contact 22. Preferably, power contact 22 is made of brass or other relatively soft and highly conductive metal. In the preferred embodiment, power element 18 is made of tungsten, which provides excellent conductive and electrosurgical cutting properties. However, tungsten is hard metal and is difficult to mate with other materials to obtain a secure electrical connection. In order to provide a good electrical connection, power contact 22 and proximal and 44 of power element 18 are connected through a constructed form joint. For example, power contact 22 may be crimped or otherwise deformed to mate with "J-hook" proximal and 44 of power element 18. Power contact 22 abuts insulated portion 42 and is sealed thereto with an epoxy. Insulated portion 42 is connected to multilumen tube 28 through return power contact 24. Return power contact 24 is connected to insulated portion 42 with a male/female connection and is sealed with an epoxy. Return power contact 24 abuts multilumen tube 28 and is sealed with an epoxy.

Return element 20 extends through multilumen tube 28 and terminates at a proximal end connecting to return power contact 24 for return of current to the power supply. Preferably, power element 18 is electrically connected to return power contact 24 through a conductive epoxy 46. As can be seen in FIG. 2, return element 20 extends through multilumen tube 28 and is directly connected to return power contact 24. This configuration eliminates any joints in the electrical path.

Persons skilled in the art will recognize that many modifications and variations are possible in the details, materials, and arrangements of the parts and actions which have been described and illustrated in order to explain the nature of this invention and that such modifications and variations do not depart from the spirit and scope of the teachings and claims contained therein.

While the inventor understands that claims are not a necessary component of a provisional patent application, and therefore has not included detailed claims, the inventor reserves the right to claim, without limitation, at least the following subject matter.

What is claimed:

1. An electrode assembly for use with an electrosurgical instrument comprising:
   an elongate flexible shaft having a proximal end and a distal end;
   a first electrode located within the shaft having a distal end and proximal end, the distal end of the first electrode being formed as a working element to apply electrical energy to a body of a patient;
   a second electrode located within the shaft having a distal end and a proximal end; the distal end of the second electrode being formed as a working element distally spaced from the first electrode, the second electrode being electrically insulated from the first electrode;
   a current return contact connected to the proximal end of the second electrode;
   a power contact located at the proximal end of the shaft directly connected to the proximal end of the first electrode, wherein the proximal end of the first electrode is affixed to the power contact with a friction fit, the power contact adapted to removably couple with a power connection for a medical instrument; and
   wherein the shaft includes separate first and second lumens, the first electrode is located in one of the first or second lumens and the second electrode is located in the other of the first and second lumens.

2. The assembly of claim 1, wherein the first electrode comprises tungsten.

3. The assembly of claim 2, wherein the proximal end of the first electrode is bent into a J-hook for a connection with the power contact.

4. The assembly of claim 2, wherein the proximal end of the first electrode is connected to the power contact by crimping.

5. The assembly of claim 4, wherein the power contact comprises brass.

6. The assembly of claim 1, wherein the second electrode is connected to the current return contact through a conductive epoxy joint.

7. The assembly of claim 1, wherein the proximal end of the shaft is constructed and arranged for connection with a power supply, wherein the first electrode is connected to the power supply at a more proximal position than the second electrode.

8. A method of making an electrode assembly for use with an electrosurgical instrument, comprising the steps of:
   providing an elongate flexible shaft having a proximal end and a distal end;

providing a first electrode located within the shaft having a distal end and a proximal end, the distal end of the first electrode being formed as a working element to apply electrical energy to a body of a patient;

providing a second electrode located within the shaft having a distal end and a proximal end; the distal end of the second electrode being formed as a working element distally spaced from the first electrode, the second electrode being electrically insulated from the first electrode;

providing a current return contact connected to the proximal end of the second electrode;

providing a power contact located at the proximal end of the shaft directly connected to the proximal end of the first electrode, wherein the proximal end of the first electrode is connected to the power contact with a friction fit, the power contact adapted to removably couple with a power connection for a medical instrument; and wherein the shaft includes separate first and second lumens, the first electrode is located in one of the first or second lumens and the second electrode is located in the other of the first and second lumens.

9. The method of claim 8, wherein the first electrode comprises tungsten.

10. The method of claim 9, further comprising forming the proximal end of the first electrode into a J-hook for connection with the power contact.

11. The method of claim 9, further comprising crimping the proximal end of the first electrode to the power contact.

12. The method of claim 8, wherein the proximal end of the shaft is constructed and arranged for connection with a power supply, wherein the first electrode is connected to the power supply at a more proximal position than the second electrode.

13. The method of claim 8, wherein the second electrode is connected to the current return contact through a conductive epoxy joint.

14. An electrode assembly for use with an electrosurgical instrument that includes a power connection for removably electrically coupling with the electrode assembly, the assembly comprising:
 a power element defining a current path between (i) a power contact for coupling with a power connection on a medical instrument and (ii) an end of the working element for electrosurgically working at a surgical site;
 a return element defining a return current path between (i) the surgical site or the working element and (ii) a return contact for current to exit the assembly;
 the power and return elements being electrically insulated from one another;
 wherein the power contact is configured and selected to couple with a power connection for a medical instrument, the power contact being formed of a first conductive material that covers an area of the power element comprising a second conductive material wherein the current path for at least the power element is free of joints;
 wherein the first material is relatively softer than the second material;
 wherein the power element and return element are each elongate elements disposed in separate lumens defined by a first layer comprising an insulating material; and
 wherein the power elements and insulating materials form a flexible construction.

15. The assembly of claim 14 wherein the power contact comprises brass and second material comprises tungsten, the tungsten area comprising a section of the power element bent back in contact with itself and covered with brass.

16. The assembly of claim 15 wherein the tungsten is bent in a substantially J-shape.

17. The assembly of claim 16 wherein the assembly is adapted to be removably coupled and used with a resectoscope.

18. An electrode assembly for use with an electrosurgical instrument that includes a power connection for removably electrically coupling with the electrode assembly, the assembly comprising;
 a power element defining a current path between (i) a power contact for coupling with a power connection on a medical instrument and (ii) an end of a working element for electrosurgically working at a surgical site;
 a return element defining a return current path between (i) the surgical site or the working element and (ii) a return content for current to exit assembly;
 the power and return elements being electrically insulated from one another;
 wherein the power contact is configured and selected to couple with a power connection for a medical instrument, the power contact being formed of a first conductive material that covers an area of the power element comprising a second conductive material wherein the current path for at least the power element is free of joints;
 wherein the first material is relatively softer that the second material; and
 wherein the power contact comprises brass and the second material comprises tungsten, the tungsten area comprising a section of the power element bent back in contact with itself and covered with brass.

* * * * *